(12) United States Patent
Haubrich et al.

(10) Patent No.: US 10,533,153 B2
(45) Date of Patent: Jan. 14, 2020

(54) PRODUCTION OF SQUALENE AND/OR STEROL FROM CELL SUSPENSIONS OF FERMENTED YEAST

(71) Applicant: SANOFI-AVENTIS DEUTSCHLAND GMBH, Frankfurt am Main (DE)

(72) Inventors: Andreas Haubrich, Frankfurt am Main (DE); Gerhard Korb, Frankfurt am Main (DE); Jean-Francois Trotzier, Paris (FR)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 280 days.

(21) Appl. No.: 14/775,564

(22) PCT Filed: Mar. 11, 2014

(86) PCT No.: PCT/EP2014/054657
§ 371 (c)(1),
(2) Date: Sep. 11, 2015

(87) PCT Pub. No.: WO2014/139989
PCT Pub. Date: Sep. 18, 2014

(65) Prior Publication Data
US 2016/0024457 A1 Jan. 28, 2016

(30) Foreign Application Priority Data
Mar. 13, 2013 (EP) ..................................... 13158937

(51) Int. Cl.
*C12N 1/06* (2006.01)
*C12P 33/00* (2006.01)
*C12P 5/00* (2006.01)

(52) U.S. Cl.
CPC .............. *C12N 1/063* (2013.01); *C12P 5/007* (2013.01); *C12P 33/00* (2013.01)

(58) Field of Classification Search
None
See application file for complete search history.

(56) References Cited

U.S. PATENT DOCUMENTS

| | | | |
|---|---|---|---|
| 5,460,823 A | 10/1995 | Jensen et al. | |
| 5,460,949 A * | 10/1995 | Saunders | C12N 9/0006 435/189 |
| 2012/0110898 A1* | 5/2012 | Malm | C11B 1/10 44/307 |
| 2014/0073037 A1 | 3/2014 | Patinier | |

FOREIGN PATENT DOCUMENTS

| | | |
|---|---|---|
| EP | 2 268 823 B1 | 1/2011 |
| FR | 2 975 705 A1 | 11/2012 |
| WO | WO-2010/023551 A2 | 3/2010 |

OTHER PUBLICATIONS

Beltran, G. et al. (Jan. 2008). "Effect of Fermentation Temperature and Culture Media on the Yeast Lipid Composition and Wine Volatile Compounds," *International Journal of Food Microbiology* 121 (2):169-177.

Bhattacharjee, P. et al. (Aug. 2003). "Extraction of Squalene from Yeast by Supercritical Carbon Dioxide," *World Journal of Microbiology & Biotechnology* 19(6):605-608.

Germann, M. et al. (Oct. 28, 2005, e-pub. Aug. 24, 2005). "Characterizing Sterol Defect Suppressors Uncovers a Novel Transcriptional Signaling Pathway Regulating Zymosterol Biosynthesis," *Journal of Biological Chemistry* 280(43):35904-35913.

Kelly G.S. (Feb. 1999). "Squalene and its Potential Clinical Uses," *Alternative Medicine Review* 4(1):29-36.

Kockmann, N. (May 2012). "Scale-up-fähiges Equipment für die Prozessentwicklung-Scalable Equipment for Process Development," *Chemie Ingenieur Technik* 84(5):646-659, (Eng. Translation of the introduction only).

Kohno, Y. et al. (Apr. 28, 1995). "Kinetic Study of Quenching Reaction of Singlet Oxygen and Scavenging Reaction of Free Radical by Squalene in N-Butanol," *Biochimica et Biophysica Acta* 1256(1):52-56.

Kuchta, T. et al. (May 1, 1997). "Inhibition of Ergosterol Biosynthesis Is Not Accompanied by a Change in Fatty Acid Composition in Saccharomyces Cerevisiae Treated With the Antifungal Agent 6-Amino-2-N-Pentylthiobenzothiazole," *FEMS Microbial. Lett* 150(1):43-47.

Leber, R. et al. (2001). "A Novel Sequence Element is Involved in the Transcriptional Regulation of Expression of the ERG1 (Squalene Epoxidase) Gene in Saccharomyces Cerevisiae," *European Journal of Biochemistry* 268(5):914-924.

Mantzouridou, F. et al. (2009). "Squalene versus Ergosterol Formation Using Saccharomyces Cerevisiae: Combined Effect of Oxygen Supply, Inoculum Size, and Fermentation Time on Yield and Selectivity of the Bioprocess," *Journal of Agriculture and Food Chemistry* 57(14):6189-6198.

Mantzouridou, F. et al. (Sep. 2010, e-pub. Jun. 11, 2010). "Observations on Squalene Accumulation in Saccharomyces Cerevisiae Due to the Manipulation of HMG2 and ERG6," *FEMS Yeast Research* 10(6):699-707.

Mountfort, K.A. et al. (Apr. 1, 2007, e-pub. Mar. 8, 2007). "Identification of Oxidation Products of Squalene in Solution and in Latent Fingerprints by ESI-MS and LC/APCI-MS," *Anal. Chem.* 79(7):2650-2657.

Paltauf, F. et al. (Aug. 18, 1982). "Squalene and Ergosterol Biosynthesis in Fungi Treated with Nafftine a New Antimycotic Agent," *Biochimica Et Biophysica Acta* 712(2):268-273.

(Continued)

*Primary Examiner* — Erin M. Bowers
(74) *Attorney, Agent, or Firm* — Morrison & Foerster LLP

(57) ABSTRACT

The present invention relates to a process for the production of squalene and/or sterol in high amounts using an alkaline solution and an organic lysis solvent at high temperature and high pressure for effectively lysing yeast cells and extracting squalene and/or sterol into an organic extraction solvent, thus obtaining squalene and/or sterol in high amount and of high purity.

14 Claims, No Drawings

(56) References Cited

OTHER PUBLICATIONS

Pasrija, R. et al. (2005, e-pub. Apr. 21, 2005). "Squalene Epoxidase Encoded by ERG1 Affects Morphogenesis and Drug Susceptibilities of Candida Albicans," *Journal of Antimicrobial Chemotherapy* 55(6):905-913.

Polakowski, T. et al. (Jan. 1998). "Overexpression of a Cytosolic Hydroxymethylglutaryl-CoA Reductase Leads to Squalene Accumulation in Yeast," *Applied Microbiology and Biotechnology* 49(1):66-71.

Ryder, N.S. et al. (May 1986). "Ergosterol Biosynthesis Inhibition by the Thiocarbamate Antifungal Agents Tolnaftate and Tolciclate," *Antimicrob. Agents Chemother.* 29(5):858-860.

Ryder, N.S. et al. (Sep. 15, 1985). "Inhibition of Squalene Epoxidase by Allylamine Antimycotic Compounds. A Comparative Study of the Fungal and Mammalian Enzymes," *Biochem. J.* 230(3):765-770.

Sanati, H. et al. (Nov. 1997). "A New Triazole, Voriconazole (UK-109,496), Blocks Sterol Biosynthesis in Candida Albicans and Candida Krusei," *Antimicrobial Agents and Chemotherapy* 41(11):2492-2496.

Shang, F. et al. (Jan. 2006). "High-Cell-Density Fermentation for Ergosterol Production by Saccharomyces Cerevisiae," *Journal of Bioscience and Bioengineering* 101(1):38-41.

Singhal, R. S. et al. (Oct. 1990). "Detection of Adultration of the Spice Poppy Seeds (*Papaver somniferum*) With *Amaranthus paniculatas* (Rajgeera) Seeds," *Journal of Food Quality* 13(5):375-381.

International Search Report dated Apr. 7, 2014 for International Application No. PCT/EP2014/054657, filed on Mar. 11, 2014, four pages.

Written Opinion of the International Searching Authority dated Apr. 7, 2014 for International Application No. PCT/EP2014/054657, filed on Mar. 11, 2014, six pages.

Bhattacharjee, P. et al. (2001). "Studies on Fermentative Production of Squalene," *World Journal of Microbiology & Biotechnology* 17:811-816, seven pages. Original Article for—Bhattacharjee, P. et al. (2002). "Study on Production of Squalene by Fermentation," *Journal of Pharmaceuticals* 4:167.

Lei, F. et al. (2011). "Analysis and Identification of Squalene from Marine Strain of Candida Tropicalis," *Guangxi Sciences* 18(2):161-163, (English Abstract only).

* cited by examiner

PRODUCTION OF SQUALENE AND/OR STEROL FROM CELL SUSPENSIONS OF FERMENTED YEAST

CROSS REFERENCE TO RELATED APPLICATIONS

This application is a National Phase application under 35 U.S.C. § 371 of International Application No. PCT/EP2014/054657 filed Mar. 11, 2014, which claims priority benefit to EP Application No. 13158937.6 filed Mar. 13, 2013, the disclosures of which are herein incorporated by reference in their entirety.

The present invention relates to the field of squalene and/or sterol and more specifically to a process for producing squalene and/or sterol in high amounts from yeast cells by lysing the yeast cells in an aqueous suspension medium at elevated pressure and high temperatures in the presence of an alkaline and an organic lysis solvent.

Squalene, a compound of Formula (I)

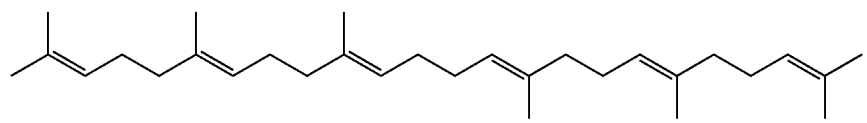

(I)

is widely distributed in nature. All plants and animals produce squalene, including humans.

It is also present in human blood serum and in foodstuffs such as olive oil, wheat germ oil and rice oil. The highest concentrations are found in shark liver oil wherein it is present in an amount of up to 90%. Squalene is industrially hydrated to squalane which serves as a basis for ointments and as lubricant or transformer oil. In the pharmaceutical field, squalene is used as an ingredient of adjuvants which are added to vaccines for enhancing the effectiveness thereof. Thereby, squalene, because of its presence in the human and animal body, is well-tolerated. For example, adjuvants comprising squalene are comprised by the vaccines Pandemrix and Celtura, which have been used in the context of vaccination against swine flu (H1N1) in 2009. Squalene has been obtained for commercial purposes primarily from shark liver oil, but plant sources (primarily vegetable oils) are used as well, including amaranth seed, rice bran, wheat germ, and olives.

Squalene with the systematic name 2,6,10,15,19,23-hexamethyltetracosa-2,6,10,14,18,22-hexaene and the molecular formula $C_{30}H_{50}$ is an unsaturated hydrocarbon from the group of triterpenes. It is a natural and vital part of the synthesis of cholesterol, steroid hormones, and vitamin D in the animal body.

Due to the safety of squalene, there will be an enhanced application of squalene in adjuvants for the development of new vaccines in the future. Pharmaceutical uses, however, require high quality squalene of high purity. Consequently, there will be an enhanced demand for squalene being present in very pure form. It is estimated that there will be demands for squalene as high as several tons per year and this amount may rise dramatically in case of a pandemia to the 10- to 20-fold of the basic amount. As squalene cannot be stored indefinitely, amounts for a pandemia have to be provided in relatively short time periods (Mountfort, K. A. et al (2007); Kohno, Y. et al. (1995)).

Moreover, squalene is not only known to be effective as an adjuvant in vaccines, but there are other potential medical fields for which squalene may prove useful as a pharmaceutical. Thus, according to Kelly (1999), squalene may prove useful as activator of cellular and non-specific immune functions, as a raw material for inhibitors of cholesterol and triglyceride biosynthesis, as potentiator of cholesterol-lowering drugs, as a sink for xenobiotics or in the treatment of a variety of cancers.

A series of documents deals with the disadvantages if squalene is obtained from animals, e.g. shark, such as the limited provision of animal resources such as shark liver oil or the risk that animal resources such as sharks may be infected with pathogens which may be transferred to humans or may produce a substance which may have adverse effects on humans. Moreover, TSE (transmissible spongiform encephalopathy) causing agents or agents causing a TSE-similar disease may exist in animal sources. Also, sharks may contain human toxins such as carchatoxins, or accumulate environmental contaminants such as pesticides.

In order to avoid adverse effects when using squalene from natural, in particular animal sources, new processes of production of squalene have been developed, comprising inter alia the fermentation of specific, optionally genetically engineered yeast cells, which produce squalene, and the isolation of squalene therefrom.

Such yeast cells can be of natural origin or can be manipulated or genetically optimized, whereby it is desired to select strains which produce squalene in high yields.

The production of squalene by fermentation of yeast cells with subsequent lysis is known for example from Mantzouridou et al. (2009) and Paltauf et al. (1982) who describe the application of mechanical lysis or disruption of cells using high pressure homogenization (HPH) resulting in high pressure differences or homogenization in the presence of beads. Singhal et al. (1990) describe a laboratory process for cell lysis. However, the processes of the prior art are disadvantageous due to high consumption of organic solvents and alkaline solutions which are used for lysis of yeast cells and extraction of squalene. Moreover, the processes of the prior art are afflicted with the further disadvantage that emulsions are formed if the amount of the organic solvent is decreased in the lysis medium. Consequently, subsequent addition of an extraction solvent and separation of the organic phase comprising squalene and the aqueous phase is possible only after several hours of standing or by centrifugation. Moreover, the methods of the prior art are economically not suitable for a continuous processing. However, if high amounts of a culture medium such as 60,000-200,000 liter or even more are to be processed, e.g. in case of a pandemia, continuous processing is advantageous.

FR-A-2 975 705 describes the isolation of squalene, without using an organic solvent, produced by 1) preparing a biomass of microalgae; 2) treating the resulting biomass using a protease enzyme and 3) centrifuging the resulting reaction mixture in order to separate the oil from the aqueous phase; and 4) recovering the thus-produced crude oil containing squalene.

Sterols are steroid alcohols and constitute a subgroup of steroids with a hydroxyl group in the 3'-position of the A-Ring. Sterols form part of the cellular membrane where they influence its fluidity and function and participate as secondary messengers in developmental signaling. Sterols are also present in microorganisms such as yeast where they are responsible for structural membrane features.

An important pharmaceutical sterol is ergosterol with the IUPAC designation ergosta-5,7,22-trien-3β-ol and the molecular formula $C_{28}H_{44}O$. Ergosterol is also a main sterol in yeast cells and is responsible for structural membrane features such as integrity, fluidity, permeability and the activity of membrane-bound enzymes. Ergosterol is the major precursor of vitamin $D_2$ and cortisone and is an important pharmaceutical intermediate that can be converted into cortisone and flavone hormones. Ergosterol is mainly produced by two different methods, one method being yeast fermentation. Several means of improving ergosterol yield from yeast include the screening of highly productive strains, the optimization of cultivation conditions and the overexpression of genes in the ergosterol biosynthesis pathway of a mutant strain. However, as above with respect to squalene, the processes of the prior art are disadvantageous for similar reasons as above, being high consumption of material and the formation of emulsions (Shang et al. (2006)).

The chemical formula of ergosterol is indicated in Formula (II).

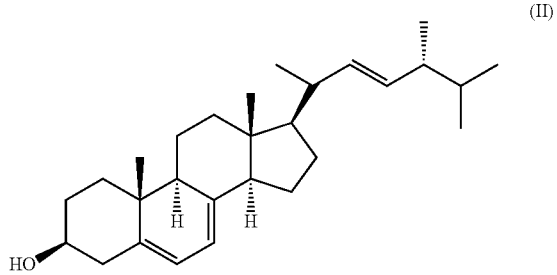

(II)

Another sterol is lanosterol, a compound of the formula (III),

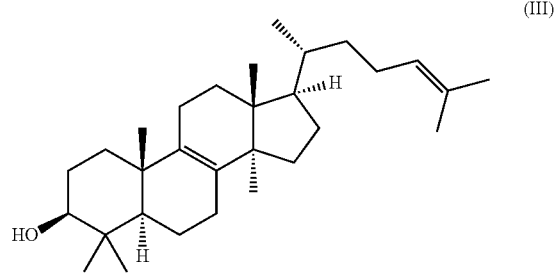 [SMILES: CC(C)=CCC[C@@H](C)[C@H]1CC[C@@]2(C)C3=C(CC[C@]12C)[C@@]1(C)CC[C@H](O)C(C)(C)[C@@H]1CC3]

(III)

which is the first sterol produced in yeasts in the biosynthesis pathway of ergosterol.

There is therefore a need in the art for a method by which high amounts of squalene and/or sterol can be produced from yeast in a cost-effective way avoiding the use of high amounts of material and of high consumption of resources (time, energy etc.) and avoiding emulsification during the production process. The problem is solved by the present invention by the provision of the claims.

The process of the present invention thereby satisfies the requirement for high amounts of squalene and/or sterol which have to be provided within shortest periods of time in high amounts, for example in the case of a pandemia if large amounts of vaccines and consequently of adjuvants comprising squalene are needed. Moreover, by using reagents in low amounts, the process of the present invention meets economic and ecological requirements.

Surprisingly, a process for the production of squalene and/or sterol was identified by which the disadvantages of high consumption of material and time and of strong emulsification can be avoided by performing lysis of yeast cells producing squalene and/or sterol at high temperatures (over the normal boiling point of the various solutions at atmospheric pressure) under elevated pressure.

By applying the process of the present invention, complete or nearly complete lysis of the yeast cells is achieved in relatively short time. The process may be performed batchwise but is also suitable for the application in a continuous mode. The selected solvent or solvents can be recycled by e.g. distillation.

In a first aspect, the present invention refers to a process for producing squalene and/or sterol lysing squalene and/or sterol containing yeast cells in a lysis medium, wherein the lysis medium comprises an aqueous suspension medium, an alkaline and an organic lysis solvent, and wherein the lysis is performed in a closed system under elevated pressure at a temperature, which is above the boiling point of the lysis medium at atmospheric pressure.

In another aspect, the present invention refers to a process for producing squalene and/or sterol comprising
(a) fermenting yeast cells in a culture medium, and
(b) lysing squalene and/or sterol containing yeast cells in a lysis medium, wherein the lysis medium comprises an aqueous suspension medium, an alkaline and an organic lysis solvent, and wherein the lysis is performed in a closed system under elevated pressure at a temperature, which is above the boiling point of the lysis medium at atmospheric pressure.

The yeast cells in step (a) are optionally separated from the culture medium and re-suspended in an appropriate aqueous suspension medium such as water. The yeast cells may as well be subjected to lysis in subsequent step (b) in the culture medium as the aqueous suspension medium. In such a case, the yeast suspension obtained in step (a) above is preferably used in step (b) without previous separation of the yeast cells from the culture medium.

The process of the present invention is characterized in high temperatures and high pressures that make possible a relatively short residence time.

As used herein, the term "process" may be understood in the widest sense as an activity, method or procedure, by which squalene and/or sterol can be produced from a yeast cell including culturing and lysis of the yeast cell.

A suitable yeast cell includes any yeast cell that produces squalene and/or sterol. Examples of yeasts suitable in the process of the present invention include species of the genus Arthroascus, Arxiozyma, Arxula, Bullera, Candida, Debaryomyces, Dekkera, Dipodascopsis, Endomyces, Eremothecium, Geotrichum, Hanseniaspora, Hansenula, Hormoascus, Issatchenkia, Kloeckera, Kluyveromyces, Lipomyces, Lodderomyces, Metschn[iota]kowia, Pachysolen, Pachytichospora, Pichia, Rhodosporidium, Rhodotorula, Saccharomyces, Saccharomycodes, Schizoblastosporion, Schizosaccharomyces, Schwaniomyces, Sporobolomyces, Sterigmatomyces, Sympodiomyces, Taphrina, Torula, Torulaspora, T[sigma]rulopsis, Trichosporon,

*Yarrowia, Zygohansenula,* and *Zygosaccharomyces*. A preferred yeast is *Saccharomyces cerevisiae*.

The sterol can be any sterol which can be produced by a yeast cell, either naturally or artificially by the introduction of the respective gene(s) which result(s) in the production of the desired sterol. Preferably, the yeast cell produces ergosterol and/or lanosterol and most preferably ergosterol.

Therefore, in a fourth aspect of the present invention, the sterol is ergosterol and/or lanosterol, preferably ergosterol.

The yeast cell may be a yeast cell which naturally produces squalene and/or sterol or may be a yeast cell which has been manipulated to produce squalene and/or sterol or to produce squalene and/or sterol to a higher extent. As squalene and/or sterol is/are produced preferably for industrial purposes, where the demands for the squalene and/or sterol are high, the yeast cell preferably produces squalene and/or sterol in a high extent, preferably squalene and/or sterol is/are present in the yeast cell in an amount of at least 1%, at least 2%, at least 5%, at least 10% or at least 15% (w/w) until 20% 25% or 30% of the dry mass (DM) of the yeast cell. Thus, a yeast strain naturally producing squalene and/or sterol in high yield may be used in the process of the present invention. For example, the wildtype strain of *Yarrowia lipolytica* produces squalene in an amount of 0.5% of cell dry weight, whereas *Saccharomyces uvarum* produces squalene in an amount of 1.4% of cell dry weight.

Moreover, for increasing the content of squalene and/or sterol in a yeast cell, the yeast may be manipulated. The skilled person knows how to manipulate a yeast cell to produce squalene and/or sterol at all or to produce an enhanced amount of squalene and/or sterol versus a yeast cell without manipulation. Manipulation of a yeast cell may be done by genetic engineering in order to introduce and express a desired gene in the yeast cell. The procedure of introducing a gene or nucleic acid into a host cell is called transformation. Transformation may be done by any method known in the art, including the use of plasmids which can be introduced into yeast cells either as replicating molecules or by integration into the genome. Elimination of genes is also well-known in the art. Alternatively, manipulation of yeast cells may be done by mutagenesis, either randomly or directed, followed by analysis of the mutagenized cells for production of squalene and/or sterol. Manipulation may be done by influencing genes encoding proteins which are involved in the metabolism of squalene and/or sterol to increase the yield thereof, e.g. by increasing the activity of enzymes involved in anabolism and/or decreasing the activity of enzymes involved in catabolism of squalene and/or sterol. Increase or decrease of the expression level of an enzyme may be obtained by introducing one or more further genes or by eliminating the respective gene; by providing a stronger or weaker promoter; by addition of a homologous or heterologous gene encoding an enzyme involved in anabolism of squalene and/or sterol, by decrease/prevention of expression of an inhibitor/suppressor or by increase of expression of an activation factor of the enzymes involved in the metabolism of squalene and/or sterol or of genes encoding such enzymes; by mutating a gene encoding an enzyme involved in the metabolism of squalene and/or sterol to enhance or decrease the activity of the enzyme. Standard methods of genetic engineering or manipulation of yeast cells are known in the art and are for example disclosed in Sambrook et al. (1989).

Homologous in the context of the present invention means that the introduced gene is already present in the cell, while heterologous in the context of the present invention means that the introduced gene is not present in the cell.

For example, yeast cells producing squalene may be manipulated for increasing production of squalene. Enzymes involved in squalene biosynthesis include mevalonate kinase, phosphomevalonate kinase, pyrophosphomevalonate decarboxylase, isopentenyl pyrophosphate isomerase, HMGR (3-hydroxy-3-methylglutaryl-CoA reductase), and squalene synthase. Genes involved in the conversion of squalene to ergosterol include squalene epoxidase (ERGI), lanosterol synthase, C14-dimethylase, d14-reductase, C4-methyloxidase, C4-decarboxylase (ERG26), 3-ketoreductase, C24-methyltransferase, C8-isomerase, C5-desaturase, d22-desaturase and d24-reductase. Other catabolic enzymes include LEU2 ([beta]-isopropylmalate dehydrogenase), oxidosqualene cyclase, zymosterol-24-methyltransferase and ergosta-5,7,24(28)-trienol-22-dehydrogenase.

The genes encoding these enzymes may be manipulated in that the activity of the respective enzymes is either increased or decreased, depending on the enzyme, to allow accumulation of squalene. Thereby, the activity of an enzyme involved in anabolism may be increased which may result a higher production of squalene. Vice versa, the activity of an enzyme involved in the catabolic pathway may be decreased to allow accumulation of squalene.

Several documents in the art deal with genetic manipulations in yeast for increasing squalene yield. For example, hyper-expression of HMGR, an anabolic enzyme, or expression of a truncated form of HMGR results in squalene accumulation (U.S. Pat. No. 5,460,949; Polakowski et al. (1998)). Also mutation of oxidosqualene cyclase (ERG7) causes squalene accumulation (Germann et al. (2005). Disruption of squalene epoxidase, a catabolic enzyme, causes accumulation of squalene (Pasrija et al. (2005)). A combination of these approaches may be used e.g. expression of cytosolic truncated HMGR in combination with knockout of squalene epoxidase. Squalene accumulation is also achieved by manipulation of the Hmg2 gene coding for HMGR2 and Erg6 gene coding for 24C-methyltransferase, which manipulation results in an increase of squalene yield of about 20 times versus the wildtype strain (Mantzouridou and Tsimidou, (2010)).

Moreover, accumulation of squalene may be achieved by the use of factors in the culture medium that manipulate the activity of enzymes involved in the metabolism of squalene in order to increase the yield of squalene. For instance, allylamine antimycotics (e.g. terbinafine, naftifine) can inhibit squalene epoxidase resulting in ergosterol deficiency and an accumulation of intracellular squalene (Ryder et al. (1985); Paltauf et al. (1982)). Terbinafine causes an increase of squalene of about 100-fold by influencing squalene epoxidases (Leber et al. (2001)). Other antimycotics that can cause squalene accumulation include, but are not limited to, voriconazole (Sanati et al. (1997)), 6-amino-2-n-pentylthio-benzothiazole (Kuchta et al. (1997)), and thiocarbamate antimycotics (e.g. tolnaftate and tolciclate) (Ryder et al. (1986)). EP 2 268 823 gives a short overview of yeast cells producing high amounts of squalene, as defined in the present invention. Such yeast cells are suitable for use in the process of the present invention.

The skilled person is aware that approaches of genetic manipulation, use of activators or inhibitors of enzymes involved in metabolism or selection of specific yeast cells are applicable for the production of a sterol. For example, screening for high producer strains and genetic manipulation of yeast cells (e.g. overexpression of the HMG1 gene coding for HMGR2, of the ERG1 gene coding for squalene epoxidase, of the ERGS gene coding for squalene synthase or otherwise named farnesyl-diphosphate farnesyltransferase and of the ERG11 gene coding for lanosterol 14-alpha demethylase) for obtaining a high ergosterol yield is already state of the art (Shang et al. (2006)).

In a further aspect of the present invention, the yeast cells produce squalene and/or sterol in high amounts, preferably at least in an amount of at least 1%, at least 2%, at least 5%, at least 10% or at least 15% (w/w) until 20%, 25% or 30% of the dry mass (DM) of the yeast cell.

The term "comprising" as used herein is meant to "include or encompass" the desired feature and further features which must not be specifically mentioned. The term "comprising" is also meant to "consist of" the desired feature and not to include further features except the desired feature. Thus, the process referred to herein may be defined by additional steps and/or features in addition to the steps and/or features as indicated herein, e.g. in addition to the indicated steps, further steps may be included which, however, are not specified herein.

The term "aqueous suspension medium" as used herein is an aqueous liquid such as water or a culture medium useful for growing or cultivating the yeast cells.

A culture medium as used herein for growing or cultivating the yeast cell is a liquid medium designed to support the growth of the yeast cell and to allow the production of squalene and/or sterol. An important distinction between growth media types is that of defined (also synthetic) versus undefined (also basal or complex) media. A defined medium will have known quantities of all ingredients. For microorganisms, they consist of providing trace elements and vitamins required by the microbe and especially a defined carbon source and nitrogen source. Minimal media are those that contain the minimum nutrients possible for colony growth, generally without the presence of amino acids, and are often used by microbiologists and geneticists to grow "wild type" microorganisms. Selective media are used for the growth of only selected microorganisms. Differential media or indicator media distinguish one microorganism type from another growing on the same media. This type of media uses the biochemical characteristics of a microorganism growing in the presence of specific nutrients or indicators (such as neutral red, phenol red, eosin, or methylene blue) added to the medium to visibly indicate the defining characteristics of a microorganism. Enriched media contain the nutrients required to support the growth of a wide variety of organisms. All these media may be used for culturing the yeast cell, as long as the yeast cell can grow in it.

In principle, any medium which allows the growth of yeast cell may be selected for culturing. Culturing is carried out in an aqueous solution, whereby the medium comprises components necessary to allow growth of the yeast cell and production of squalene and/or sterol. The skilled person thereby knows or is capable of identifying those components which are necessary for the growth of the microorganism and the production of squalene and/or sterol. The medium should comprise any nutrients which are necessary for the growth of the yeast cell and the production of squalene and/or sterol. Essential nutrients comprise assimilable carbon sources, assimilable nitrogen sources and minerals and, if necessary, growth factors or other useful factors.

As assimilable carbon source a series of carbohydrates may be used, as long as they can be used by the yeast cell. Useable carbon sources are glucose, sucrose, lactose, dextrins, starch, molasses, or sugar alcohols such as glycerol, mannitol or sorbitol. The carbohydrates are present altogether preferably in an amount of 5 to 70 g/l, more preferably in an amount of 10 to 50 g/l, most preferably in an amount of 20 to 30 g/l.

As assimilable nitrogen source, substances such as nitrate, anorganic or organic ammonium salts, urea and amino acids, or more complex substances such as proteins such as casein, lactalbumin, gluten or the hydrolysates thereof or soybean flour, fish meal, meat extract, yeast extract, distillers' soluble, corn steep liquor or corn steep solid may be used. The nitrogen sources are present altogether preferably in an amount of 5 to 50 g/l, more preferably in an amount of 10 to 25 g/l, most preferably in an amount of 12 to 20 g/l.

As minerals, alkali or alkaline earth salts such as alkali or alkaline earth chloride, carbonate, phosphate or sulfate are usable. Examples of alkali or alkaline earth metals are sodium, calcium, zinc, cobalt, iron, copper and manganese salts. The salts are preferably present altogether in an amount of 1 to 25 g/l.

If necessary for the growth of the yeast cell, other factors may be included. The skilled person knows or will be able to elucidate which factors are to be used to allow growth of the yeast cell and production of squalene and/or sterol.

The pH value of the culture medium is selected to allow the growth of the yeast cell and the production of squalene and/or sterol. Preferably, the medium has a pH of 6 to 8, more preferably the medium has a pH of 7.

The yeast cell is incubated in the culture medium at a temperature suitable for the growth of the yeast cell and the production of squalene and/or sterol. Preferably, the temperature is between 0 and 50° C., more preferably between 10 and 45° C., even more preferably between 20 and 40° C. and still more preferably 30° C.

Typically, the duration of the culture is between one hour and 250 hours, preferably 30 to 200 hours and more preferably 45 to 170 hours. The reaction time depends on the yeast cell used. Advantageous and optimal culturing times can be easily determined by those skilled in the art.

Typical culture media include YPD (Yeast Extract Peptone Dextrose; 1% yeast extract, 2% peptone, 2% glucose); YPDS (1% yeast extract, 2% peptone, 2% glucose, 1 M sorbitol); Sabouraud's dextrose broth (2% dextrose, 1% peptone, pH 5.6); YCM (yeast complete medium, 1% neo-peptone, 1% yeast extract, 0.05% $KH_2PO_4$, 2% glucose), YPG (yeast extract peptone galactose, 1% yeast extract, 2% peptone, and 2% galactose); YPGS (YPGS medium is YPD medium containing 5% galactose and 0.2% sucrose instead of 2% glucose); YT (0.8% bacto-tryptone, 0.5% yeast extract, 0.5% NaCl, pH 7, adjust with NaOH); YAPD (2% peptone, 2% glucose, 1% yeast extract, 0.01% adenine); SD (0.17% yeast nitrogen base without amino acids, 2% glucose); YPL (1% yeast extract, 2% peptone, 2% lactate) or YEP (1% yeast extract, 1% peptone, 0.5% NaCl, pH 7.0).

For the purposes of the present invention, a culture medium is a medium into which a yeast cell is inoculated and which supports the growth of the yeast cell and the production of squalene and/or sterol.

The production of squalene and/or a desired sterol by fermentation can be manipulated by the skilled person by the selection of a specific culture medium and specific culture conditions such as temperature, aeration or culturing duration. Beltran et al. (2008) describe the influence of culture medium and fermentation temperature on the amounts of squalene and specific sterols. For example, squalene contents have been found to be higher in synthetic medium versus natural medium such as grape must. Lanosterol levels have been found to be similar in synthetic medium and natural medium such as grape must, whereas ergosterol levels have been found to be higher in natural medium such as grape must. Moreover, the proportion of squalene increases with longer incubation times and at higher temperatures (25° C. versus 13° C.). Mantzouridou et al. (2009) show that the type of yeast strain, aeration strategy, inoculum size and stage of growth cycle are critical factors for squalene and ergosterol yield. A yeast dry weight of 120 g/l and an ergosterol yield of 1500 mg/l was obtained in a 5 l fermenter under conditions of 30° C., pH 5.5, 600 rpm agitation speed, 60 h fermentation time, ethanol concentration below 1% and respiratory quotient at about 1.0 (Shang et al. (2006)). In order to increase the production of squalene, a two-stage culture system may be used including culturing under aerobic conditions to enhance biomass and then switching to anaerobic conditions after entering of the yeast cell into the lag phase to increase squalene production. Thus, depending on the compound which is produced by the process of the present invention, the skilled person will be able to select suitable culturing media and conditions for obtaining maximum production of squalene and/or the selected sterol.

The culturing may be carried out in any volume useful for the production of squalene and/or sterol by the yeast cell. The scale may be in the laboratory scale in the μl to ml range, in the scale of shake flask cultivation with a scale of 5 ml to 500 ml to several liters such as 2 l, 5 l or 20-30 l or in the scale of bioreactors with a scale of at least 50 l. The scale is therefore in the range of some microliters to thousands of liters such as 10 μl to 1,000,000 liter. As the present invention is directed to the production of squalene and/or sterol for industrial purposes, the scale is preferably in the range of 50 l to 1000,000 l, more preferably of 60,000 to 200,000 l.

A variety of assays is known in the art by which the skilled person may detect a compound and determine the concentration of the compound. Explicitly mentioned are radiometric assays which measure the incorporation of radioactivity into substances or its release from substances. The radioactive isotopes most frequently used in these assays are $^{14}C$, $^{32}P$, $^{35}S$ and $^{125}I$. The concentration may also be determined by Western analysis or an ELISA assay using an antibody or antiserum against the tested compound. Chromatographic assays measure product formation by separating the reaction mixture into its components by chromatography. This is usually done by high-performance liquid chromatography (HPLC), but one can also use the simpler technique of thin layer chromatography. Although this approach can need a lot of material, its sensitivity can be increased by labeling the substrates/products with a radioactive or fluorescent tag. A preferred method is quantification by HPLC/MS. Liquid chromatography-mass spectrometry (LC-MS, or alternatively HPLC-MS) is an analytical chemistry technique that combines the physical separation capabilities of liquid chromatography (or HPLC) with the mass analysis capabilities of mass spectrometry. LC-MS is a powerful technique used for many applications which has very high sensitivity and specificity. The term "mass spectrometry" refers to the use of a ionization source to generate gas phase ions from a sample on a surface and detecting the gas phase ions with a mass spectrometer. The term "laser desorption mass spectrometry" refers to the use of a laser as a ionization source to generate gas phase ions from a sample on a surface and detecting the gas phase ions with a mass spectrometer. A preferred method of mass spectrometry for biomolecules such as acylated acyl acceptor is matrix-assisted laser desorption/ionization mass spectrometry or MALDI. Another preferred method is surface-enhanced laser desorption/ionization mass spectrometry or SELDI. In mass spectrometry the "apparent molecular mass" refers to the molecular mass (in Daltons)-to-charge value, m/z, of the detected ions. In combination with HPLC the analyte is ionized by diverse API techniques such as ESI (elektrospray ionization) or APCI (atmospheric pressure chemical ionization). In the analyser, the ions are separated according to their mass-to-charge m/z ratio. Other methods are GC (gas chromatography), GC/MS (gas chromatography coupled to mass spectrometry), utraviolet (UV) spectroscopy, infrared spectroscopy (IR) and nuclear magnetic resonance (NMR).

In the context of the present invention, the term "lysis" or "cell lysis" refers to the disintegration of the yeast cells in the aqueous suspension medium, whereby yeast cells break down to cell debris and biological molecules including proteins, DNA, RNA and lipids from the inside of a cell are released into the medium. Due to the high costs of growing cells, an effective lysis of the cells is desired and necessary to ensure that the maximum of squalene and/or sterol is released into the medium and can be recovered therefrom.

For effecting lysis of the cultured yeast cells, a yeast suspension including the cultured yeast cells and the lysis medium are mixed and lysis is allowed to be effected at a given temperature over a given time period.

In the context of the present invention, "lysis medium" is the aqueous suspension medium, an alkaline and an organic lysis solvent. The "lysis mixture" is the mixture of the yeast cells and the lysis medium.

The "alkaline" may be any solid alkaline or alkaline solution which is suitable, in combination with the organic lysis solvent, to effect lysis of yeast cells, preferably the alkaline is an alkali or alkaline earth hydroxide and more preferably potassium hydroxide (KOH), sodium hydroxide (NaOH), lithium hydroxide (LiOH), calcium hydroxide (Ca(OH)$_2$), magnesium hydroxide (Mg(OH)$_2$), caesium hydroxide (CsOH) or barium hydroxide (Ba(OH)$_2$). Still more preferably, the alkaline is potassium hydroxide, sodium hydroxide or lithium hydroxide. Most preferably, the alkaline is solid potassium hydroxide, e.g. in the form of pellets, or the alkaline is a potassium hydroxide solution.

The amount of the alkaline compound in the lysis mixture is indicated herein as the amount of the alkaline in gram related to the amount of dry mass (DM) of yeast cells in gram. The amount of the alkaline may vary. With respect to potassium hydroxide, the amount may be from 0.1 to 5.0 gram per gram dry mass of yeast cells and is preferably 0.2 to 3.0 gram.

The dry mass (DM) of the yeast cells may be determined by any method known in the art and includes gravimetric methods which are used for the quantitative determination of an analyte based on the mass of a solid or spectroscopic measurement of turbidity and association thereof with dry cell weight.

The organic lysis solvent may be any organic solvent which is suitable, in combination with the alkaline, to effect lysis of yeast cells. The solvent is preferably a polar protic solvent such as ethanol, methanol, n-butanol, isopropanol or n-propanol. Most preferably, the solvent is ethanol.

The amount of the organic lysis solvent in the lysis medium is indicated herein as the amount of the solvent in gram related to the amount of dry mass (DM) of yeast cells in gram. The amount of the organic lysis solvent may vary. With respect to ethanol, the amount may be from 1 to 20 gram per gram dry mass of yeast cells and is preferably 3 to 12 gram and more preferably 5 to 8 gram. Most preferably, ethanol is present in an amount of 5.2 to 6.4 g/g DM of yeast cells. This corresponds to 22 mmol to 435 mmol, preferably 65 mmol to 261 mmol, more preferably 109 mmol to 174 mmol and most preferably 113 mmol to 139 mmol per gram dry mass of yeast cells, respectively. If organic lysis solvents other than ethanol are used, the skilled person will be able to adapt the amounts as indicated above for ethanol to other organic lysis solvents and thus, to determine amounts of the other organic lysis solvents which are suitable for the processes of the present invention. For example, other organic lysis solvents such as methanol, n-butanol, isopropanol or n-propanol may be used in an amount of 22 mmol to 435 mmol, preferably 65 mmol to 261 mmol, more preferably 109 mmol to 174 mmol and most preferably 113 mmol to 139 mmol per gram dry mass of yeast cells.

In a further aspect, the present invention relates to process, wherein the temperature is at least 30° C. above the normal boiling point of the lysis mixture at atmospheric pressure, preferably 40 to 150° C. above the normal boiling point of the lysis mixture and most preferably 70 to 95° C. above the normal boiling point of the lysis mixture.

As used herein, the term "temperature, which is above the normal boiling point of the lysis mixture at atmospheric pressure" may be understood in the sense, that the temperature of the lysis mixture is related to the normal boiling point of that suspension which forms if the yeast cells, the aqueous suspension medium, the alkaline and the organic lysis solvent are mixed. If, for example, an aqueous suspension medium with a normal boiling point around 100° C., an aqueous potassium hydroxide solution with a normal boiling point around 100° C. and ethanol with a normal boiling point around 80° C. are used as the lysis medium, then it may be assumed that the normal boiling point of the resulting lysis mixture may be between the highest and lowest normal boiling points of the suspension medium, the alkaline and the organic lysis solvent, being in that example 80 to 100° C. The normal boiling point of a solution can be determined by a person skilled in the art having regard to the definition of normal boiling point, as indicated below. If the normal boiling point of the lysis mixture is unclear or cannot be determined, then the skilled person who wants to carry out the invention may use a temperature for lysis of the yeast cells which is above the normal boiling point of that liquid out of aqueous suspension medium, alkaline and organic lysis solvent which has the highest normal boiling point. For example, with regard to the preferred embodiment of the present invention wherein the alkaline is a potassium hydroxide solution and the organic lysis solvent is ethanol, lysis may be performed at a temperature of above 100° C., preferably of at least about 100° C.+30° C., i.e. at least about 130° C. More preferably, the temperature of lysis is 40° C. to 150° C. above the normal boiling point of the lysis mixture, in the example above this would be 140° C. to 250° C., and most preferably 70° C. to 95° C. above the normal boiling point of the lysis mixture, in the example above this would be 170° C. to 195° C.

The normal boiling point of the lysis mixture is assumed to be about 100° C. The normal boiling points of such suspensions are known to the skilled person or can be easily determined experimentally. The normal boiling point of organic solvents used as the organic lysis solvents in the process of the present invention are known to the skilled person or the skilled person is able to determine them experimentally. For example, the normal boiling points of ethanol, methanol, n-butanol, isopropanol or n-propanol are as indicated in the following table:

TABLE 1

| Organic lysis solvent | Normal boiling point |
| --- | --- |
| Ethanol | 79° C. |
| Methanol | 65° C. |
| n-Butanol | 118° C. |
| Isopropanol | 82° C. |
| n-Propanol | 97° C. |

The normal boiling point of a substance is the temperature at which the vapor pressure of the liquid equals the pressure surrounding the liquid and the liquid changes into a vapor. A liquid in a vacuum has a lower boiling point than when that liquid is at atmospheric pressure. A liquid at high pressure has a higher boiling point than when that liquid is at atmospheric pressure. In other words, the normal boiling point of a liquid varies depending upon the surrounding environmental pressure. For a given pressure, different liquids boil at different temperatures. The normal boiling point (also called the atmospheric boiling point or the atmospheric pressure boiling point) of a liquid is the special case in which the vapor pressure of the liquid equals the defined atmospheric pressure at sea level, 1 atmosphere. At that temperature, the vapor pressure of the liquid becomes sufficient to overcome atmospheric pressure and allows bubbles of vapor to form inside the bulk of the liquid. The normal boiling point is now (as of 1982) defined by IUPAC as the temperature at which boiling occurs under a pressure of 1 bar ($1 \times 10^5$ Pa). Thus, if the skilled person wants to determine the normal boiling point at atmospheric pressure, he/she has to heat the solution under the pressure of 1 bar until the solution is bubbling.

In a further aspect, the present invention relates to a process, wherein lysis is effected at a pressure at which vaporization of the lysis medium is prevented, preferably at 2 to 50 bar (2 to $50 \times 10^5$ Pa) more preferably at 3 to 40 bar (3 to $40 \times 10^5$ Pa), even more preferably at 6 to 30 bar (6 to $30 \times 10^5$ Pa) at a temperature, which is above the boiling point of the lysis medium at ambient pressure and corresponds to the pressure according to the vapor pressure curve of the lysis mixture. Lysis of yeast cells is effected in the process of the present invention at a pressure at which vaporization of the lysis medium is prevented. Vapor pressure of a liquid is determined by the temperature. The vapor pressure of a liquid is the pressure exerted by a vapor in thermodynamic equilibrium with its condensed phases at a given temperature in a closed system. The equilibrium vapor pressure is an indication of the evaporation rate of a liquid. It relates to the tendency of particles to escape from the liquid. The vapor pressure of a substance increases non-linearly with temperature. A vapor pressure curve presents the vapor pressure of a liquid dependent on its temperature. At higher temperature, the vapor pressure is higher than at lower temperature. In order to avoid vaporization of the lysis medium at a temperature as used in the lysis step of the present invention, the pressure has to be increased. This allows heating of the liquid above its normal boiling point. Thereby, a higher temperature of the liquid results a higher pressure. If the pressure is too low, the liquid would vaporize.

In the present invention, the temperature of the lysis mixture is at least 30° C., preferably 40 to 150° C. and more preferably 70 to 95° C. above the normal boiling point of the obtained mixture of the yeast suspension, the alkaline solution and the organic lysis solvent at atmospheric pressure. In order to avoid vaporization of the lysis mixture at the above temperatures, a pressure which is above the vapor pressure of the lysis mixture at a specific temperature has to be applied. The pressure is built up by performing the lysis in a closed system while subjecting the lysis mixture to an increased temperature.

Thus, the pressure depends on the temperature of the lysis mixture and increases with increasing temperature. Consequently, in a preferred embodiment the lysis is performed at 115 to 270° C. and at a pressure of 2 to 50 bar (2 to $50 \times 10^5$ Pa), preferably at 140 to 250° C. and a pressure of 3 to 40 bar (3 to $40 \times 10^5$ Pa), more preferably 6 to 40 bar (6 to $40 \times 10^5$ Pa), and more preferably at 170 to 195° C. and 6 to 30 bar (6 to $30 \times 10^5$ Pa), more preferably at 12 to 20 bar (12 to $20 \times 10^5$ Pa).

By using the process of the present invention, lysis of the yeast cells is performed within a relatively short period of time. A "relatively short period of time" is meant within the concept of the present invention to be a time period of 1 to 140 minutes, more preferably 1 to 60 minutes, still more preferably 1 to 20 minutes, still more preferably 1 to 10 minutes and most preferably 3 to 5 minutes.

Therefore, a further aspect the present invention relates to a process, wherein the lysis is effected within a time period of 1 to 140 minutes, more preferably 1 to 60 minutes, still more preferably 1 to 20 minutes, still more preferably 1 to 10 minutes and most preferably 3 to 5 minutes.

The Examples indicate lysis times of 3 to 5 minutes, which are sufficient to effect complete or nearly complete lysis of the cultured yeast cells in the presence of potassium hydroxide and ethanol at a temperature of 170 to 195° C. (the pressure applied in the Examples is thus 12 to 20 bar (12 to $20 \times 10^5$ Pa). The skilled person will be aware that the minimal lysis time to achieve complete lysis is dependent on the kind and amount of alkaline and organic lysis solvent used and the temperature applied. Thus, for performing the process of the invention, the skilled person may adapt the alkaline and the organic lysis solvent and their amounts and the temperature in order to obtain a relatively short time period for complete or nearly complete lysis of the cells. Thereby, decreasing the lysis temperature within the scope of the invention will prolong the time period, until complete or nearly complete lysis is obtained, whereas increase of temperature will shorten the reaction time at which complete or nearly complete lysis occurs.

In this respect, the process of the present invention is characterized by the fact that, due to the selection of lysis temperatures being above the normal boiling point of the obtained lysis mixture, the amounts of alkaline and organic lysis solvent versus the amount of the aqueous suspension medium can be kept at low levels for effecting lysis, as compared to the amounts used in the prior art (see e.g. Comparative Examples). Thus, while the amounts of alkaline and organic lysis solvent can be varied in order to achieve complete or nearly complete lysis of the cultured yeast cells, this should not be done at the costs of using too high amounts of alkaline and organic lysis solvent. Given the information herein, the skilled person will be able to determine which alkaline and/or organic lysis solvents may be used at which temperature in order to achieve complete or nearly complete lysis of the cultured yeast cells in the most effective way.

In order to obtain a maximum yield of squalene and/or sterol from the yeast cells, it is necessary that lysis is maximally performed. The processes as comprised herein using an alkaline and an organic lysis solvent at the indicated temperature for effecting lysis have been found to be effective as a degree of lysis is obtained which is complete or nearly complete. Thereby, a complete or nearly complete lysis is effected if at least 90%, at least 93%, at least 95%, at least 97%, at least 99% or at least 99.5%, and preferably 100% of the yeast cells in the lysis mixture are disrupted and their content is released into the lysis medium. This does not only relate to the destruction of the cell membrane, but also to the destruction of organelle membranes, so that also the compounds comprised therein are released into the culture medium. Consequently, a complete or nearly complete lysis is effected if at least 90%, at least 93%, at least 95%, at least 97%, at least 99% or at least 99.5%, and preferably 100% of squalene and/or sterol present in the yeast cells are released into the lysis medium.

The completeness of cell lysis can be evaluated by any method known in the art. For example, cell lysis can be evaluated by optical means by visualizing the cells under the microscope or by determining solid particles via measuring changes in electrical resistance with a Coulter counter. Other means include determination of the squalene and/sterol concentration in the lysis medium after lysis has occurred. Another method involves the determination of cell survival, which is, however, time consuming.

The present invention is characterized by the fact that a complete or nearly complete lysis of the yeast cell is effected by the use of an alkaline and an organic lysis solvent, avoiding the application of mechanical lysis or disruption of cells using high pressure homogenization (HPH) resulting in high pressure differences or homogenization in the presence of beads. Mechanical lysis or disruption of cells under the application of pressure would be required to be performed for several times, which is time and cost intensive. Moreover, the procedures of the prior art use a filtration step following lysis and before extraction. Also such filtration step is not needed and applied in the present lysis procedure.

In a further embodiment, the lysis step as comprised by the process of the present invention is achieved by mixing a suspension of yeast cells in an aqueous suspension medium with an alkaline and an organic lysis solvent, whereby a lysis mixture is formed, and subjecting the lysis mixture to a temperature, which is above the normal boiling point of the lysis mixture, and under elevated pressure and without the need to apply additional means such as mechanical means for effecting lysis.

In a further embodiment, the extraction of the lysis mixture is performed without filtration.

In a further embodiment, the process of the present invention is characterized in that the yeast cell is cultured in a culture medium to result in a yeast suspension, and the yeast suspension comprising the cultured yeast cells and the culture medium (as the aqueous suspension medium) is mixed with the alkaline and the organic lysis solvent at a given temperature and pressure as outlined above to effect lysis of the yeast cells.

The yeast cells used in the process of the present invention can be grown using any known culture or fermentation system. The yeast cells may be cultured in a discontinuous or continuous mode. In the discontinuous mode (batch mode), the yeast cells grow and yeast products are produced in a closed system until the rate of growth is limited. Yeast cells and nutrients are usually added at the beginning of the culture and left for a period of time. The cells are no longer in the growth phase, but are in the stationary phase. In the discontinuous mode, temperature is controlled during culturing. Usually, in biotechnology the discontinuous or batch fermentation is the fermentation of choice, due to the better operability in case of contamination or mutation of fermented microorganisms.

In the continuous mode, nutrients are added and product is removed, so that culturing is in a steady state. The yeast cells are at the exponential growth phase. Nutrient and product levels should be kept at constant levels.

In the present invention, culturing of the yeast cells may be performed in a discontinuous or continuous mode. The process of the present invention can ideally be adapted to the continuous fermentation mode. Therefore, in a preferred embodiment, the yeast cells are grown in the process of the present invention in a continuous mode and are cultured in a continuous bio-reactor.

Lysis of the cultured yeast cells may be performed in a continuous or discontinuous reactor. Thereby, the continuous mode is preferred. In a particularly preferred embodiment, culturing and lysis are performed in the continuous mode. For lysis, the flows of yeast suspension, alkaline and organic lysis solvent are dosed into a continuously working reactor. Thereby, the flows can be charged separately or dosed into the reactor after mixing. Alternatively, the flows of alkaline and organic lysis solvent are dosed into a reactor already harbouring the yeast suspension. The dosing into the continuously working reactor may be in such a manner that the residence time in the reactor is within a time period which is sufficient to allow complete or nearly complete lysis of the yeast cells, preferably 1 to 140 minutes, more preferably 1 to 60 minutes, still more preferably 1 to 20 minutes, still more preferably 1 to 10 minutes and most preferably 3 to 5 minutes. The temperature and pressure of the lysis mixture is as indicated above.

The alkaline and the organic lysis solvent, be they mixed or not, may be pre-heated before being added to the yeast suspension. Pre-heating may be performed by applying a process-integrated heat exchange between the hot lysis mixture after lysis has occurred and a cold culture medium and/or a cold yeast suspension and/or a cold alkaline solution and/or a cold organic lysis solvent, which are to be used in a subsequent culturing and/or lysis step. The continuous mode for culturing and/or lysing yeast cells, preferably for culturing and lysis, is suitably used in a process in which squalene and/or sterol is/are produced at industrial level in high yields amounting to yields in the ton range. In Kockmann (2012), the application and scale-up strategy of continuous-flow micro-structured reactors are disclosed. Examples of reactors for continuous culturing and/or lysing useful in the present invention are a flow-through reactor with or without stirring, whereby the reaction vessel is with or without a static mixer. Suitable stirrers are disc stirrer, impeller stirrer, propeller stirrer etc. Other suitable reactors are bed reactors such as a fluidized bed reactor.

The admixture of the alkaline and the organic lysis solvent to the suspension of the yeast cells in the suspension medium may be performed in the same continuous reaction system as the culturing, preferably if the suspension medium is the culturing medium.

In a further aspect, the present invention relates to a process comprising
(a) lysing squalene and/or sterol containing yeast cells in a lysis medium, wherein the lysis medium comprises an aqueous suspension medium, an alkaline and an organic lysis solvent, and wherein the lysis is performed in a closed system under elevated pressure at a temperature, which is above the boiling point of the lysis medium at atmospheric pressure,
(b) adding an organic extraction solvent to the lysed yeast mixture, and
(c) isolating squalene and/or sterol from the organic extraction solvent phase.

In a further aspect, the present invention relates to a process comprising
(a) fermenting yeast cells in a culture medium,
(b) lysing squalene and/or sterol containing yeast cells in a lysis medium, wherein the lysis medium comprises an aqueous suspension medium, an alkaline and an organic lysis solvent, and wherein the lysis is performed in a closed system under elevated pressure at a temperature, which is above the boiling point of the lysis medium at atmospheric pressure,
(c) adding an organic extraction solvent to the lysed yeast mixture, and
(d) isolating squalene and/or sterol from the organic extraction solvent phase.

The "organic extraction solvent" may be any organic solvent which is suitable to extract squalene and/or sterol from the lysis mixture after lysis, preferably after complete or nearly complete lysis has occurred. The organic extraction solvent is preferably a non-polar solvent, preferably a halogenated or preferably non-halogenated (i) alkane such as heptane, more preferred n-heptane or an isomer mixture of heptane (iso-heptane), pentane, hexane, petrol ether or chloroform, (ii) cycloalkane, such as cyclohexane, (iii) aromat, such as benzene, toluene or xylol, (iv) ketone, such as methyl-isobutyl-ketone (MIBK), or (v) ether, such as diethylether, particularly n-heptane or iso-heptane. The organic extraction solvent may also be a mixture of solvents such as a mixture of the afore-mentioned solvents, for example of hexane, n-heptane and/or iso-heptane. Most preferably, the organic extraction solvent is heptane, still more preferably n-heptane or iso-heptane, for the production of squalene.

There exist nine isomers of heptane being n-heptane, 2-methylhexane, 3-methylhexane, 2,2-dimethylpentane, 2,3-dimethylpentane, 2,4-dimethylpentane, 3,3-dimethylpentane, 3-ethylpentane and 2,2,3-trimethylbutane. The term "iso-heptane" is an isomer mixture of heptane and is meant to comprise any combination of any isomer of heptane, e.g. each of the nine isomers are used as the organic extraction solvent or two, three, four, five, six, seven or eight out of the nine isomers of heptane are used as the organic extraction solvent.

The amount of the organic extraction solvent versus the lysis mixture is indicated herein as the amount of the organic extraction solvent in gram related to the amount of dry mass (DM) of yeast cells in gram. The amount of the organic extraction solvent is such that a maximum extraction of squalene and/or sterol is achieved. With respect to heptane, the amount may be from 1 to 20 gram per gram dry mass of yeast cells and is preferably 2 to 8 gram per gram dry mass of yeast cells. If organic extraction solvents other than heptane are used, the skilled person will be able to adapt the amounts as indicated above for heptane to other organic extraction solvents and thus, to determine amounts of organic extraction solvents which are suitable for the processes of the present invention. For example, other organic extraction solvents such as pentane, benzene, toluene or dietylether may be used in an amount of 1 g to 20 g, preferably 2 g to 8 g per gram dry mass of yeast cells.

The extraction degree of squalene and/or sterol, i.e. the degree at which squalene and/or sterol present in the lysis mixture is/are transferred into the organic extraction solvent according to the present invention is preferably at least 80%, more preferably at least 85%, still more preferably at least 88%, still more preferably at least 92%, still more preferably at least 94% and most preferably at least 95%.

In a preferred embodiment of the present invention the alkaline is potassium hydroxide, the organic lysis solvent is ethanol and the organic extraction solvent is n-heptane or iso-heptane. In a further preferred embodiment, the alkaline is potassium hydroxide, the organic lysis solvent is ethanol and the organic extraction solvent is n-heptane or iso-heptane and the extraction degree of squalene and/or sterol is preferably at least 80%, more preferably at least 85%, still more preferably at least 88%, still more preferably at least 92%, still more preferably at least 94%, and most preferably at least 95%.

In a further aspect, the extraction is performed with n-heptane or iso-heptane as the organic extraction solvent at a temperature of 40 to 75° C.

After completion of lysis, processing of the lysis mixture generally occurs as follows: After cooling of the lysis mixture to a temperature between 40 and 140° C., preferably 40 to 75° C., the organic extraction solvent is added, whereby squalene and/or sterol is/are extracted into the organic phase preferably within about 10 minutes, more preferably about 5 minutes. In a preferred embodiment, the organic extraction solvent is pre-warmed to a temperature of 40 to 75° C., optionally by using the waste heat of the lysis apparatus. There is no need to pre-heat the organic extraction solvent. However, in case extraction is to be performed at a temperature of 40 to 75° C., then the lysed yeast mixture plus the organic extraction medium has to be heated. Alternatively, the organic extraction solvent may be added to the hot lysis mixture during or after lysis, so that the squalene and/or sterol compounds released during or after lysis are immediately extracted into the organic extraction solvent, and cooling may be allowed to occur during or before the subsequent processing steps. In a further alternative, the organic extraction solvent is added to the hot lysis mixture during or after lysis and the extraction is performed continuously and without cooling.

The retention time within a phase separation unit or the phase separation time in a batch reactor may be 1 to 10 minutes, preferably 1 to 5 minutes. For separation of the phases, it is sufficient that the medium is allowed to stand. No centrifugation or other type of means to effect a phase separation is necessary, however, the skilled person may apply such additional means, if deemed necessary. Extraction using the organic extraction solvent may be performed as a one-step extraction, wherein the organic extraction solvent is added to the lysis medium once and the phases are separated or as a two-step or higher step extraction, wherein extraction and separation are performed more than once. In the case of a two-step or higher step extraction, extraction and phase separation times are as indicated above. There are no changes of extraction times and phase separation times.

As indicated above, the amount of the alkaline in the lysis mixture may be 1.7 mmol to 89 mmol, preferably 3.4 mmol to 54 mmol and more preferably 5.4 mmol to 36 mmol potassium hydroxide per gram dry mass of yeast cells and the amount of the organic lysis solvent in the lysis medium may be 22 mmol to 435 mmol, preferably 65 mmol to 261 mmol, more preferably 109 mmol to 174 mmol and most preferably 113 mmol to 139 mmol per gram dry mass of yeast cells. With respect to potassium hydroxide which is the preferred alkaline compound, the amount may be 0.1 to 5.0 gram, preferably 0.2 to 3.0 gram and more preferably 0.3 to 2.03 g per gram dry mass of yeast cells. With respect to ethanol as the organic lysis solvent, the amount may be 1 to 20 gram, preferably 3 to 12 gram and more preferably 5 to 8 gram per gram dry mass of yeast cells. By using the amounts of the alkaline, in particular of potassium hydroxide, or by using the amounts of the alkaline and of the organic lysis solvent, as indicated above, in particular of potassium hydroxide and ethanol, an extremely rapid phase separation is obtained in the extraction step, whereby emulsification is prevented. The retention or phase separation times may be 1 to 10 minutes, preferably 1 to 5 minutes. The velocity of phase separation is a decisive feature of the present invention. Another decisive feature is the prevention of emulsification. The present inventors have found that by the use of an alkaline and an organic lysis solvent in the amounts as indicated above a rapid phase separation is obtained. Thereby, the use of the organic lysis solvents, as indicated above, in particular of ethanol, facilitates phase separation of the aqueous and organic phases in the subsequent extraction step by dissociation of ester and amide bonds. Such a rapid phase separation cannot be obtained by increasing pressure during extraction. Thus, the advantages of the method of the present invention being rapid phase separation and prevention of emulsification are based on the use of the alkaline compound and the organic lysis solvent as indicated above.

The extraction may be performed in a continuous reactor. Thereby, the organic extraction solvent may be added to the lysis mixture during or after lysis, i.e. the organic extraction solvent flow is dosed into a continuously working reactor together with the flow or flows of alkaline and organic lysis solvent. The compounds of interest, i.e. squalene and/or sterol, that are released from the lysed yeast cells are immediately extracted into the organic extraction solvent. Extraction may also be allowed to take place in the discontinuous mode, however, the continuous mode is preferred.

Due to the rapid phase separation, phase separation may be performed in the continuous mode. Thereby, after dosing of the organic extraction solvent into the lysis mixture and extraction of squalene and/or sterol into the organic extraction solvent, the solvent is removed in a continuous mode from the reactor.

For minimizing energy supply of the production process of squalene and/or sterol, a process-integrated heat exchange may be performed. Thereby, the hot lysis mixture is cooled by simultaneously heating other solutions in a direct heat exchange procedure. Another possibility of minimizing energy supply is the renaturation of the organic solvent, i.e. the organic lysis solvent and/or the organic extraction solvent, which can be obtained in a continuous distillation process. The obtained organic solvent can be applied in a cycling process.

Squalene and/or sterol can be isolated from the organic extraction solvent by any method known in the art. Generally, the organic extraction solvent phase comprising the squalene and/or sterol product is separated from the aqueous lysis phase, the organic extraction solvent is evaporated and the resulting raw squalene and/or sterol product is further purified by distillation.

The degree of purity of squalene and/or sterol is ideally at least 95%, at least 97%, at least 98%, at least 99%, at least 99.5% and most preferably 100%.

Squalene and/or sterol thus obtained is/are highly pure and may be used for any purpose which is known in the art. This is especially desirable for application of squalene and/or sterol in humans. With respect to squalene or ergosterol, some application fields are indicated in the introductory part of the specification. Squalene produced according to the process of the present invention can be used as adjuvant in vaccines, as activator of cellular and non-specific immune functions, as inhibitor of cholesterol and triglyceride biosynthesis, as potentiator of cholesterol-lowering drugs, as a sink for xenobiotics or in the treatment of a variety of cancers.

In a further aspect, the present invention refers to a process for producing squalene as outlined above comprising lysing a aqueous suspension of squalene containing yeast cells by the addition of a potassium hydroxide solution or potassium hydroxide pellets and ethanol to the yeast suspension, whereby the lysis is performed in a closed system at a temperature of 140 to 250° C. at a pressure of 3 to 40 bar (3 to $40\times10^5$ Pa), preferably at 6 to 40 bar (6 to $40\times10^5$ Pa).

In a further aspect, the present invention refers to a process for producing squalene as outlined above comprising
(a) culturing a yeast cell producing squalene in a culture medium to result in a yeast suspension, and
(b) lysing the yeast suspension obtained in step (a) by the addition of a potassium hydroxide solution or potassium hydroxide pellets and ethanol to the yeast suspension, whereby the lysis is performed in a closed system at a temperature of 140 to 250° C. at a pressure of 3 to 40 bar (3 to $40\times10^5$ Pa), preferably at a pressure of 6 to 40 bar (6 to $40\times10^5$ Pa).

In a further aspect, the present invention refers to a process for producing squalene as outlined above, wherein the yeast cells are cultured under continuous conditions.

In a further aspect, the present invention refers to a process for producing squalene as outlined above, wherein the yeast cells are lysed under continuous conditions.

The comments and statements made above with respect to general and preferred embodiments of the process of the present invention also refer to the more preferred aspects of the present invention.

EXAMPLES

The following is an analysis of processes of the prior art for obtaining squalene from fermented yeast cells using potassium hydroxide and ethanol as lysis agents and hexane, heptane or petrol ether (petroleum) as organic extraction solvent. The processes of the prior art are compared with the process of the present invention.

Example 1

Comparative Example: Lyophilization

Comparative example 1 refers to the document of Mantzouridou et al. (2009) disclosing the production of squalene by yeast cells. Therein, yields of 5 g/l squalene are obtained in the culture medium. After fermentation, squalene is obtained by the following process steps:
1) Yeast cells are isolated by centrifugation,
2) yeast cells are washed twice with water,
3) yeast cells are lyophilized,
4) portion of dried biomass of 96 mg is added to 5 ml 60% (w/v) KOH solution in water, 7.5 ml methanol and 7.5 ml of a methanolic pyrogallol solution (0.5% w/v),
5) incubation in shaking apparatus at 45° C. overnight,
6) lipidic components are extracted three times with 10 ml hexane for each extraction, whereby phase separations are performed by centrifugation at 4000 g during 10 min,
7) optionally formed emulsions are eliminated by addition of 0.5 ml methanol,
8) the hexane fractions are dried over sodium sulfate, and
9) the solvent is then removed by 40° C. under vacuum.

The following characteristics for the process can be determined in view of the indications of the amounts above. In the following, the used amounts of crude material relative to the yeast dry mass (DM) are indicated

TABLE 2

| Material | Factor (g/g DM) |
|---|---|
| KOH | 50 |
| EtOH | 119.8 |
| Hexane | 212.5 |

Example 2

Comparative Example: Homogenization with Glass Beads

Comparative example 2 refers to the document of Paltauf et al. (1982), disclosing a laboratory process for cell lysis. The following aspects are notable:
1) Yeast cells are separated after cultivation, suspended in water and disintegrated by shaking in a homogenizer in the presence of glass beads,
2) 2 ml ethanol and 2 ml (30% (w/v)) potassium hydroxide are added to an aliquot of total lipids (about 5 mg) and the mixture is stirred by 80° C. for 60 min,
3) non-saponifiable lipids are extracted twice with 4 ml petroleum each, and
4) the obtained extract is washed twice with 2 ml water each.

The following characteristics for the process can be determined in view of the indications of the amounts above. In the following, the used amounts of crude material relative to the yeast dry mass are indicated

TABLE 3

| Material | Factor (g/g DM) |
|---|---|
| KOH | 154.7 |
| EtOH | 316 |
| Heptane | 1088 |

Example 3

Comparative Example

Comparative example 3 refers to the document of Singhal et al. (1990) describing a laboratory process for cell lysis. The following aspects are notable:
1) Soxhlet extraction by petrol ether (60-80° C. boiling point) as solvent
2) the resulting lipid is saponified: for saponification 60% (w/v) KOH and 20 ml ethanol are added to 1.0 g lipid and the reaction is heated under reflux for 30 min
3) non-saponifiable lipids are extracted by petrol ether
4) purification by chromatographic means.

The following characteristics for the process can be determined in view of the indications of the amounts above. In the following, the used amounts of crude material relative to the yeast dry mass are indicated

TABLE 4

| Material | Factor (g/g DM) |
| --- | --- |
| KOH | Not specified |
| EtOH | 15.8 |
| Petrol ether | Not specified |

Example 4

General Procedure

The following is an analysis of the processes of the present invention for obtaining squalene from fermented yeast cells using potassium hydroxide and ethanol as lysis agents and heptane as organic extraction solvent in the amounts and under the conditions as referred to above. The data allow a comparison with prior art data.

Lysis of Yeast Cells

For working with the continuously working reactor the following flows,
1) Yeast suspension,
2) Potassium hydroxide aqueous solution (50% (w/v)), and
3) Ethanol (95% (v/v)),
can be separately used or dosed to the reactor after mixing. The mixture is dosed to the continuously working reactor in a mode that the residence time is kept at 3-5 min. The working temperature is between 170 and 195° C. and thus at a pressure of about 12 to 20 bar (12 to $20 \times 10^5$ Pa).

Extraction with Heptane (n-Heptane or a Mixture of Heptane Isomers)

The processing of the lysis fractions occurs stepwise or continuously. After cooling of the reaction mixture to a temperature range of 50-66° C., 50 ml heptane per 125 g dry cell mass yeast suspension are dosed parallel to the reaction mixture, whereby squalene is extracted into the organic phase within about 5 minutes. After a coalescence time of 1-5 min the phases are separated.

The extraction can also be performed in a two step/several step extraction procedure. There are no changes of the extraction and phase separation times.

Alternatively, the extraction medium can also be added directly to the lysis process.

The resulting yield of squalene in the organic phase is in the range of 88-95% (w/w).

Example 5

The individual material flows were pre-mixed, so that the mass proportions as indicated in table 5 could be obtained. A medium residence time of 3 min was set up. The subsequent extraction was performed according to the indications in the general part of the examples.

TABLE 5

| KOH (g/g DM) | EtOH (g/g DM) | Heptane (g/g DM) | Extraction degree (%) |
| --- | --- | --- | --- |
| 0.35 | 5.54 | 3.6 | 88 |

The term "extraction degree" means that the given percentage of the total amount of squalene is identified in the extraction solvent; the remaining amount remains in the aqueous phase.

Example 6

The individual material flows were pre-mixed, so that the mass proportions as indicated in table 6 could be obtained. A medium residence time of 5 min was set up. The subsequent extraction was performed according to the indications in the chapter General Example.

TABLE 6

| KOH (g/g DM) | EtOH (g/g DM) | Heptane (g/g DM) | Extraction degree (%) |
| --- | --- | --- | --- |
| 0.33 | 5.22 | 3.6 | 91 |

Example 7

The individual material flows were pre-mixed, so that the mass proportions as indicated in table 7 could be obtained. A medium residence time of 3 min was set up. The subsequent extraction was performed according to the indications in the introductory part of the examples.

TABLE 7

| KOH (g/g DM) | EtOH (g/g DM) | Heptane (g/g DM) | Extraction degree (%) |
| --- | --- | --- | --- |
| 1.02 | 5.39 | 3.6 | 95 |

Example 8

The individual material flows were pre-mixed, so that the mass proportions as indicated in table 8 could be obtained. A medium residence time of 5 min was set up. The subsequent extraction was performed according to the indications in the introductory part of the examples.

TABLE 8

| KOH (g/g DM) | EtOH (g/g DM) | Heptane (g/g DM) | Extraction degree (%) |
| --- | --- | --- | --- |
| 1.19 | 6.32 | 3.6 | 95 |

Example 9

The individual material flows were pre-mixed, so that the mass proportions as indicated in table 9 could be obtained. A medium residence time of 3 min was set up. The subsequent extraction was performed according to the indications in the introductory part of the examples.

TABLE 9

| KOH (g/g DM) | EtOH (g/g DM) | Heptane (g/g DM) | Extraction degree (%) |
| --- | --- | --- | --- |
| 2.02 | 5.27 | 3.6 | 92 |

Example 10

The individual material flows were pre-mixed, so that the mass proportions as indicated in table 10 could be obtained. A medium residence time of 5 min was set up. The subsequent extraction was performed according to the indications in the introductory part of the examples.

TABLE 10

| KOH (g/g DM) | EtOH (g/g DM) | Heptane (g/g DM) | Extraction degree (%) |
|---|---|---|---|
| 2.03 | 5.3 | 3.6 | 94 |

As can be seen from the above, the processes of the prior art are disadvantageous due to the high consumption of solvent, basic solution and organic extraction compound. Moreover, the processes of the prior art are afflicted with the disadvantages that emulsions are formed if the amounts of alcohol is decreased. Consequently, subsequent separating of organic and aqueous phase is possible after several hours of standing or by using centrifugation. Moreover, the methods of the prior art are not suitable for a continuous processing of a reactor. However, continuous processing is necessary in order to process amounts of a culture medium as high as 60,000-200,000 liter, according to the size of the reactor, e.g. in case of a pandemia. In order to economically run a continuously working reactor, the residence times of the single steps of the processes have to be in the range of 1-30 minutes.

CITED DOCUMENTS

EP 2 268 823
U.S. Pat. No. 5,460,823
FR-A-2 975 705
Bhattacharjee P. and Singhal R. S., World Journal of Microbiology & Biotechnology 19: 605-608 (2003)
Beltran G. et al., International Journal of Food Microbiology 121: 169-177 (2008)
Germann et al., J. Biol. Chem. 280:35904-35913 (2005)
Kelly G. S., Alternative Medicine Review 4: 29-36 (1999)
Kockmann N., Chemie Ingenieur Technik 84: 646-659 (2012)
Kohno Y. et al. Biochimica et Biophysica Acta 1256: 52-56 (1995)
Kuchta et al., FEMS Microbiol. Lett. 150: 43-47 (1997)
Leber et al. European Journal of Biochemistry 286: 914-924 (2001)
Mantzourido F. et al., J. Agr. Food. Chem. 57: 6189-6198 (2009)
Mantzourido F. and Tsimidou M. Z., FEMS Yeast Res. 10: 699-707 (2010)
Mountfort K. A. et al., Anal. Chem. 79: 2650-2657 (2007)
Paltauf F. et al., Biochimica et Biophysica Acta, Lipids and Metabolism 712 (2): 268-273 (1982)
Pasrija et al., J. Antimicrob. Chemother. 55:905-913 (2005)
Polakowski et al., Appl. Microbiol. Biotechnol. 49:66-71 (1998)
Ryder et al., Biochem. J. 230: 765-770 (1985)
Ryder et al., Antimicrob. Agents Chemother. 20: 858-860 (1986)
Sambrook J, Fritsch E. F. and Maniatis T., Molecular cloning: a laboratory manual. Cold Spring Harbor Press. Cold Spring Harbor (1989)
Singhal R. S. et al., Journal of Food Quality 13, 375-381 (1990)
Sanati et al., Antimicrob. Agents Chemother. 41: 2492-2496 (1997)
Shang F. et al., Journal of Bioscience and Bioengineering 101: 38-41 (2006)

The invention claimed is:

1. A process for producing squalene comprising
   a) preparing squalene containing yeast cells by fermentation in a culture medium under batch conditions or under continuous conditions;
   b) lysing the squalene containing yeast cells in a lysis medium without mechanical lysis or disruption of cells and without separation of yeast cells from culture medium,
   wherein the lysis medium comprises the culture medium, potassium hydroxide (KOH) and a polar protic organic lysis solvent,
   and wherein the lysis is performed in a closed system under elevated pressure of 2 to 50 bar (2 to $50 \times 10^5$ Pa) and at a temperature of 140-250° C.;
   c) adding an non-polar organic extraction solvent to the lysis medium and extracting squalene from the lysis medium; and
   d) isolating squalene from the organic phase by cooling of the mixture and phase separation of organic extraction solvent phase comprising the squalene product from the lysis medium;
   wherein the lysis in b), extraction in c) and isolation in d) are performed under continuous conditions.

2. The process according to claim 1, wherein the organic lysis solvent is ethanol, methanol, n-butanol, isopropanol or n-propanol.

3. The process according to claim 1, wherein lysis is effected at a pressure at 6 to 40 bar (6 to $40 \times 10^5$ Pa).

4. The process according to claim 1, wherein the temperature is 170 to 195° C.

5. The process according to claim 1, wherein the lysis is effected within a time period of 1 to 140 minutes.

6. The process according to claim 1, wherein
   the potassium hydroxide is solid potassium hydroxide or potassium hydroxide solution,
   the organic lysis solvent is ethanol, and
   the lysis is performed under continuous conditions at a temperature of 140 to 250° C.

7. The process according to claim 1, wherein the organic extraction solvent is a halogenated or non-halogenated (i) alkane, (ii) cycloalkane, (iii) aromat, (iv) ketone, or (v) ether.

8. The process according to claim 7, wherein the organic extraction solvent is a non-halogenated alkane.

9. The process according to claim 1, wherein extraction is performed at a temperature of 40 to 140° C.

10. The process according to claim 9, wherein the extraction is performed at a temperature of 50 to 70° C.

11. The process according to claim 1, wherein the isolation of the squalene further comprises distillation of the organic extraction solvent phase in order to evaporate the organic extraction solvent and/or distillation of the squalene.

12. The process according to claim 11, wherein the distillation of the organic extraction solvent phase in order to evaporate the organic extraction solvent and/or distillation of the squalene is performed under continuous conditions with the lysis in b), extraction in c) and isolation in d).

13. The process according to claim 1, wherein the lysis is effected within a time period of 1 to 20 minutes.

14. The process according to claim 1, wherein the lysis medium comprises 0.1 to 5.0 gram KOH per gram dry mass of yeast cells.

* * * * *